(12) United States Patent
Veasey et al.

(10) Patent No.: US 7,918,832 B2
(45) Date of Patent: Apr. 5, 2011

(54) DRIVE MECHANISMS SUITABLE FOR USE IN DRUG DELIVERY DEVICES

(75) Inventors: Robert Frederick Veasey, Leamington Spa (GB); Christopher John Jones, Bidford-on-Avon (GB)

(73) Assignee: DCA Design International Ltd., Warwick (GB)

( * ) Notice: Subject to any disclaimer, the term of this patent is extended or adjusted under 35 U.S.C. 154(b) by 0 days.

(21) Appl. No.: 10/820,047

(22) Filed: Apr. 8, 2004

(65) Prior Publication Data
US 2005/0004529 A1 Jan. 6, 2005

(30) Foreign Application Priority Data
Apr. 10, 2003 (GB) .................................. 0308267.4

(51) Int. Cl.
*A61M 5/00* (2006.01)
(52) U.S. Cl. ........................................................ 604/207
(58) Field of Classification Search .......... 604/207–211, 604/187, 189
See application file for complete search history.

(56) References Cited

U.S. PATENT DOCUMENTS

| | | | |
|---|---|---|---|
| 4,470,317 A | 9/1984 | Sabloewski et al. | |
| 4,479,516 A * | 10/1984 | Hunter | 15/22.1 |
| 4,498,904 A | 2/1985 | Turner et al. | |
| 4,568,335 A | 2/1986 | Updike et al. | |
| 4,585,439 A | 4/1986 | Michel | |
| 4,833,379 A | 5/1989 | Kaibel et al. | |
| 4,865,591 A | 9/1989 | Sams | |
| 4,883,472 A | 11/1989 | Michel | |
| 4,919,596 A | 4/1990 | Slate et al. | |
| 4,936,833 A | 6/1990 | Sams | |
| 4,973,318 A | 11/1990 | Holm et al. | |
| 4,994,033 A | 2/1991 | Shockey et al. | |
| 5,017,190 A | 5/1991 | Simon et al. | |
| 5,112,317 A | 5/1992 | Michel | |
| 5,207,752 A | 5/1993 | Sorenson et al. | |
| 5,226,895 A | 7/1993 | Harris | |
| 5,246,417 A | 9/1993 | Haak et al. | |

(Continued)

FOREIGN PATENT DOCUMENTS
DE           36 09 555           9/1987
(Continued)

OTHER PUBLICATIONS

Reissue U.S. Appl. No. 10/442,855, "Injection Syringe", filed May 21, 2003, including as-filed specification, drawings, abstract, and claims, as well as the reissue declaration and a list of documents found in image file wrapper as of Aug. 6, 2009 (42 pages total).

(Continued)

*Primary Examiner* — Nicholas D Lucchesi
*Assistant Examiner* — Theodore J Stigell
(74) *Attorney, Agent, or Firm* — McDonnell Boehnen Hulbert & Berghoff LLP (57) ABSTRACT

A drive mechanism for use in a drug delivery device comprising an epicyclic gearbox. This drive mechanism includes a housing having a helical thread; a piston rod having a non-circular cross section and an external helical thread; a dose dial sleeve, which is threadedly engaged with the housing and being rotatable with respect to the housing; and a drive sleeve, located between the housing and the piston rod, which is threadedly engaged with the piston rod.

15 Claims, 4 Drawing Sheets

U.S. PATENT DOCUMENTS

| | | |
|---|---|---|
| 5,257,987 A | 11/1993 | Athayde et al. |
| 5,271,527 A | 12/1993 | Haber et al. |
| 5,279,585 A | 1/1994 | Balkwill |
| 5,279,586 A | 1/1994 | Balkwill |
| 5,281,198 A | 1/1994 | Haber et al. |
| 5,304,152 A | 4/1994 | Sams |
| 5,308,340 A | 5/1994 | Harris |
| 5,314,412 A | 5/1994 | Rex |
| 5,318,540 A | 6/1994 | Athayde et al. |
| 5,320,609 A | 6/1994 | Haber et al. |
| 5,331,954 A | 7/1994 | Rex et al. |
| 5,370,629 A | 12/1994 | Michel et al. |
| 5,383,865 A | 1/1995 | Michel |
| 5,440,976 A | 8/1995 | Giuliano et al. |
| 5,445,606 A | 8/1995 | Haak et al. |
| 5,447,150 A | 9/1995 | Bacon |
| 5,478,316 A | 12/1995 | Bitdinger et al. |
| 5,480,387 A | 1/1996 | Gabriel et al. |
| 5,492,534 A | 2/1996 | Athayde et al. |
| 5,505,704 A | 4/1996 | Pawelka et al. |
| 5,546,932 A | 8/1996 | Galli |
| 5,549,575 A | 8/1996 | Giambattista et al. |
| 5,584,815 A | 12/1996 | Pawelka et al. |
| 5,591,136 A | 1/1997 | Gabriel |
| 5,599,314 A | 2/1997 | Neill |
| 5,611,783 A | 3/1997 | Mikkelsen |
| 5,626,566 A | 5/1997 | Petersen et al. |
| 5,645,052 A | 7/1997 | Kersey |
| 5,674,204 A | 10/1997 | Chanoch |
| 5,679,111 A | 10/1997 | Hjertman et al. |
| 5,681,285 A | 10/1997 | Ford et al. |
| 5,688,251 A | 11/1997 | Chanoch |
| 5,709,662 A | 1/1998 | Olive et al. |
| 5,716,990 A | 2/1998 | Bagshawe et al. |
| 5,725,508 A | 3/1998 | Chanoch et al. |
| 5,743,889 A | 4/1998 | Sams |
| 5,755,692 A | 5/1998 | Manicom |
| 5,800,388 A | 9/1998 | Schiff et al. |
| 5,823,998 A | 10/1998 | Yamagata |
| 5,843,036 A | 12/1998 | Olive et al. |
| 5,882,718 A | 3/1999 | Pommer et al. |
| 5,898,028 A | 4/1999 | Jensen et al. |
| 5,921,966 A | 7/1999 | Bendek et al. |
| 5,928,201 A | 7/1999 | Poulsen et al. |
| 5,947,934 A | 9/1999 | Hansen et al. |
| 5,951,530 A | 9/1999 | Steengaard et al. |
| 5,954,689 A | 9/1999 | Poulsen |
| 5,961,496 A | 10/1999 | Nielsen et al. |
| 5,980,491 A | 11/1999 | Hansen |
| 5,984,900 A | 11/1999 | Mikkelsen |
| 6,003,736 A | 12/1999 | Ljunggren |
| 6,004,297 A * | 12/1999 | Steenfeldt-Jensen et al. ............ 604/207 |
| 6,010,485 A | 1/2000 | Buch-Rasmussen et al. |
| 6,033,376 A | 3/2000 | Rockley |
| 6,033,377 A | 3/2000 | Rasmussen et al. |
| 6,074,372 A | 6/2000 | Hansen |
| 6,083,197 A | 7/2000 | Umbaugh |
| 6,106,501 A | 8/2000 | Michel |
| 6,110,149 A | 8/2000 | Klitgaard et al. |
| 6,129,080 A | 10/2000 | Pitcher et al. |
| 6,146,361 A | 11/2000 | DiBiasi et al. |
| 6,193,698 B1 | 2/2001 | Kirchhofer et al. |
| 6,221,046 B1 | 4/2001 | Burroughs et al. |
| 6,221,053 B1 | 4/2001 | Walters et al. |
| 6,231,540 B1 | 5/2001 | Smedegaard |
| 6,235,004 B1 * | 5/2001 | Steenfeldt-Jensen et al. ............ 604/207 |
| 6,248,090 B1 | 6/2001 | Jensen et al. |
| 6,248,095 B1 | 6/2001 | Giambattista et al. |
| 6,258,062 B1 | 7/2001 | Thielen et al. |
| 6,269,340 B1 | 7/2001 | Ford et al. |
| 6,277,097 B1 | 8/2001 | Mikkelsen et al. |
| 6,277,098 B1 | 8/2001 | Klitmose et al. |
| 6,281,225 B1 | 8/2001 | Hearst et al. |
| 6,283,941 B1 | 9/2001 | Schoenfeld et al. |
| 6,287,283 B1 | 9/2001 | Ljunggreen et al. |
| 6,302,869 B1 | 10/2001 | Klitgaard |
| 6,312,413 B1 | 11/2001 | Jensen et al. |
| 6,340,357 B1 | 1/2002 | Poulsen et al. |
| 6,364,860 B1 | 4/2002 | Steck et al. |
| 6,514,230 B1 | 2/2003 | Munk et al. |
| 6,547,763 B2 | 4/2003 | Steenfeldt-Jensen et al. |
| 6,547,764 B2 | 4/2003 | Larsen et al. |
| 6,562,011 B1 | 5/2003 | Buch-Rasmussen et al. |
| 6,569,126 B1 | 5/2003 | Poulsen et al. |
| 6,582,404 B1 | 6/2003 | Klitgaard et al. |
| 6,605,067 B1 | 8/2003 | Larsen |
| 6,613,019 B2 | 9/2003 | Munk |
| 6,663,602 B2 | 12/2003 | Møller |
| 6,692,472 B2 | 2/2004 | Hansen et al. |
| 6,716,198 B2 | 4/2004 | Larsen |
| 6,726,661 B2 | 4/2004 | Munk et al. |
| 6,770,288 B2 | 8/2004 | Duirs |
| 6,796,970 B1 | 9/2004 | Klitmose et al. |
| 6,893,415 B2 | 5/2005 | Madsen et al. |
| 6,899,698 B2 | 5/2005 | Sams |
| 6,899,699 B2 | 5/2005 | Enggaard |
| 6,932,794 B2 | 8/2005 | Giambattista et al. |
| 6,945,961 B2 | 9/2005 | Miller et al. |
| 7,008,399 B2 | 3/2006 | Larsen et al. |
| 7,090,662 B2 | 8/2006 | Wimpenny et al. |
| 7,094,221 B2 | 8/2006 | Veasey et al. |
| 7,104,972 B2 | 9/2006 | Moller et al. |
| 7,133,329 B2 | 11/2006 | Skyggebjerg et al. |
| 7,175,055 B2 | 2/2007 | Hansen et al. |
| 7,241,278 B2 | 7/2007 | Moller |
| 7,316,670 B2 | 1/2008 | Graf et al. |
| 7,553,299 B2 | 6/2009 | Veasey et al. |
| 2002/0029018 A1 | 3/2002 | Jeffrey |
| 2002/0052578 A1 * | 5/2002 | Moller .................. 604/208 |
| 2002/0077852 A1 | 6/2002 | Ford et al. |
| 2002/0120235 A1 | 8/2002 | Enggaard |
| 2002/0165499 A1 | 11/2002 | Slate et al. |
| 2003/0039679 A1 | 2/2003 | Duirs |
| 2003/0050609 A1 | 3/2003 | Sams |
| 2003/0172924 A1 | 9/2003 | Staniforth et al. |
| 2004/0059299 A1 | 3/2004 | Moller et al. |
| 2004/0186431 A1 | 9/2004 | Graf et al. |
| 2004/0210199 A1 | 10/2004 | Atterbury et al. |
| 2004/0236282 A1 | 11/2004 | Braithwaite |
| 2004/0249348 A1 | 12/2004 | Wimpenny et al. |
| 2004/0260247 A1 | 12/2004 | Veasey et al. |
| 2004/0267207 A1 | 12/2004 | Veasey et al. |
| 2004/0267208 A1 | 12/2004 | Veasey et al. |
| 2005/0019400 A1 | 1/2005 | Deveney et al. |
| 2005/0033244 A1 | 2/2005 | Veasey et al. |
| 2005/0055011 A1 | 3/2005 | Enggaard |
| 2005/0113765 A1 | 5/2005 | Veasey et al. |
| 2005/0205083 A1 | 9/2005 | Staniforth et al. |
| 2005/0209570 A1 | 9/2005 | Moller |
| 2005/0268915 A1 | 12/2005 | Wassenaar et al. |
| 2006/0264839 A1 | 11/2006 | Veasey et al. |
| 2007/0093761 A1 | 4/2007 | Veasey et al. |

FOREIGN PATENT DOCUMENTS

| | | |
|---|---|---|
| DE | 3814023 A1 | 1/1989 |
| EP | 0 295 075 B1 | 12/1988 |
| EP | 0 615 762 B1 | 9/1994 |
| EP | 0 554 996 B1 | 10/1996 |
| EP | 0 673 482 B1 | 4/1998 |
| EP | 0 937 471 A2 | 8/1999 |
| EP | 0 937 476 A2 | 8/1999 |
| EP | 0 937 476 A3 | 8/1999 |
| EP | 0 937 477 A2 | 8/1999 |
| EP | 1 294 418 | 7/2005 |
| FR | 2 583 291 | 12/1986 |
| FR | 2 767 479 | 2/1999 |
| JP | 05-337179 A | 12/1993 |
| JP | 06-296691 A | 10/1994 |
| RU | 2 111 019 | 5/1998 |
| WO | WO 90/09202 | 8/1990 |
| WO | WO 91/10460 | 7/1991 |
| WO | WO 91/14467 A1 | 10/1991 |
| WO | WO 96/25965 A1 | 8/1996 |
| WO | WO 96/26754 A | 9/1996 |

| | | |
|---|---|---|
| WO | WO 98/57688 | 12/1998 |
| WO | WO 99/16487 | 4/1999 |
| WO | WO 99/38554 A1 | 8/1999 |
| WO | WO 01/10484 A1 | 2/2001 |
| WO | 01/95959 A1 | 12/2001 |
| WO | WO 02/76535 A1 | 3/2002 |
| WO | WO 02/053214 A1 | 7/2002 |
| WO | WO 02076535 A1 * | 10/2002 |
| WO | WO 02/092153 A2 | 11/2002 |

OTHER PUBLICATIONS

Reissue U.S. Appl. No. 10/960,900, "Injection Syringe", filed Oct. 7, 2004, including as-filed specification, drawings, abstract, and claims, as well as the reissue declaration and a list of documents found in image file wrapper as of Aug. 6, 2009 (37 pages total).

Reissue U.S. Appl. No. 11/121,331, "Injection Syringe", filed May 3, 2005, including as-filed specification, drawings, abstract, and claims, as well as the reissue declaration and a list of documents found in image file wrapper as of Aug. 6, 2009 (35 pages total).

Reissue U.S. Appl. No. 11/640,610, "Injection Syringe", filed Dec. 18, 2006, including as-filed specification, drawings, abstract, and claims, as well as the reissue declaration and a list of documents found in image file wrapper as of Aug. 6, 2009 (29 pages total).

* cited by examiner

DRIVE MECHANISMS SUITABLE FOR USE IN DRUG DELIVERY DEVICES

THE TECHNICAL FIELD OF THE INVENTION

The present invention relates to drive mechanisms suitable for use in drug delivery devices, in particular pen-type injectors, having dosage setting means, enabling the administration of medicinal products from a multidose cartridge. In particular, the present invention relates to such drug delivery devices where a user may set the dose.

DESCRIPTION OF RELATED ART

Such drug delivery devices have application where regular injection by persons without formal medical training occurs, i.e., patients. This is increasingly common amongst those having diabetes where self-treatment enables such persons to conduct effective management of their diabetes.

These circumstances set a number of requirements for drug delivery devices of this kind. The device must be robust in construction, yet easy to use in terms of the manipulation of the parts, understanding by a user of its operation and the delivery of the required dose of medicament. Dose setting must be easy and unambiguous. In the case of those with diabetes, many users will be physically infirm and may also have impaired vision requiring the drive mechanism to have low dispensing force and an easy to read dose setting display. Where the device is to be disposable rather than reusable, the device should be cheap to manufacture and easy to dispose of (preferably being suitable for recycling). To meet these requirements the number of parts required to assemble the device and the number of material types the device is made from need to be kept to a minimum.

User operated drug delivery devices are well known within the medical field.

WO 01/95959 discloses an injection device for the injection of set doses of medicine from a cartridge. The disclosed device comprises a gear wheel gearbox located between a nut, threadedly coupled to a piston rod, and an injection button. The gearbox provides a gearing ratio equal to the ratio of the second pitch of the dose setting drum to the first pitch of the piston rod.

Surprisingly it was found that the drive mechanism according to instant invention provides a valuable technical alternative for the design of a compact drive mechanism, which allows for a wide range (resp., high value) of reduction ratios between actuation and delivery, further providing the advantage of safe dose dialing and dispensing. In addition, the relatively low number of components reduces manufacturing and assembly efforts. Furthermore, the drive mechanism according to instant invention has the advantage of allowing intuitive and easy to use correction of a set dose without loss of medicament.

DESCRIPTION OF THE INVENTION

According to a first aspect of the present invention, a drive mechanism for use in a drug delivery device is provided, comprising an epicyclic gearbox, preferably a drive mechanism for use in a drug delivery device comprising a housing having a helical thread;

a dose dial sleeve, which is threadedly engaged with said housing and being rotatable with respect to said housing;

a piston rod having a non-circular cross section and an external helical thread;

a drive sleeve, located between said housing and said piston rod, which is threadedly engaged with said piston rod, characterised by further comprising an epicyclic gearbox, in particular by further comprising an epicyclic gearbox, that releasibly connects said dose dial sleeve to said drive sleeve.

The term "drug delivery device" according to instant invention shall mean a single-dose or multi-dose, disposable or re-useable device designed to dispense a selected dose of a medicinal product, preferably multiple selected doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device may comprise a needle or may be needle-free. In particular, the term "drug delivery device" shall mean a disposable multi-dose pen-type device having mechanical and manual dose delivery and dose selection mechanisms, which is designed for regular use by persons without formal medical training such as patients. Preferably, the drug delivery device is of the injector-type.

The term "housing" according to instant invention shall preferably mean any exterior housing ("main housing", "body", "shell") or interior housing ("insert", "inner body"). The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge from which a number of doses of a medicinal product may by dispensed.

The term "engaged" according to instant invention shall particularly mean the interlocking of two or more components of the drive mechanism/drug delivery device, e.g. a spline or thread connection, preferably the interlocking of helical threads of components ("threadedly engaged").

The term "helical thread" according to instant invention shall preferably mean a full or part thread, e.g., a cylindrical spiral rib/groove, located on the internal and/or external surface of a component of the drug delivery device, having an essentially triangular or square or rounded section designed to allow continuous free rotational and/or axial movement between components. Optionally, said thread may be further designed to prevent rotational or axial movement of certain components in one direction.

The term "dose dial sleeve" according to instant invention shall mean an essentially tubular component of essentially circular cross-section preferably comprising a first part of smaller diameter and a second part of a larger diameter, preferably the first part and the second part are connected by a radially extending annular region of the dose dial sleeve. In a preferred embodiment the diameter of the second part of the dose dial sleeve is the same as that of the housing. In yet another preferred embodiment the dose dial sleeve is designed to indicate a selected dose of a dispensable product. This may be achieved by use of markings, symbols, numerals, etc., e.g. printed on the external surface of the dose dial sleeve or an odometer, or the like.

In a more particular embodiment the inner surface of the second part of the dose dial sleeve is provided with splines in the form of longitudinally extending gear teeth designed to engage with the epicyclic gearbox.

In still a further embodiment the outer surface of the second part of the dose dial sleeve is provided with a textured surface to serve as a finger grip to assist in the dialing of the dose.

The term "drive sleeve" according to instant invention shall mean any essentially tubular component of essentially circular cross-section and which is engaged with the piston rod. Preferably, the drive sleeve of instant invention carries the planetary gear of the epicyclic gear box in a journal. In a preferred embodiment the drive sleeve comprises a first part of smaller diameter located between the cylindrical portion of the insert and the piston rod and a second part of larger diameter extending beyond the inwardly directed flange of the dose dial sleeve. In yet a further preferred embodiment a radially extending annular region of the drive sleeve connects the first part and the second part of the drive sleeve.

The term "piston rod" according to instant invention shall mean any component adapted to operate through/within the housing, designed to translate axial movement through/within the drug delivery device, preferably from the drive sleeve to the piston, for the purpose of discharging/dispensing an injectable product. Said piston rod may be flexible or not. It may comprise a simple rod, a lead-screw, a rack and pinion system, a worm gear system, or the like. The piston rod of instant invention may be made of any suitable material known by the person skilled in the art.

The term "releasably connected" according to instant invention shall preferably mean that two components of instant mechanism or device are reversibly joined to each other, which allows coupling and decoupling, e.g. by means of a clutch.

The term "epicyclic gearbox" according to instant invention shall mean a system of gears, comprising of a central sun gear ("sun gear") and one or more planetary gear, and a ring gear. Generally, in such an epicyclic gearbox, the planetary gear(s) travel(s) around the sun gear, whose axis is fixed. Additionally, the axis of the ring gear in such an epicyclic gearbox is identical to the fixed axis of the sun gear. The "ring gear" according to instant invention may optionally encompass a circular arrangement of splines or the like.

Preferably the epicyclic gearbox according to instant invention shall serve to transmit the torque from the dose dial sleeve or the dose button to the drive sleeve or the piston rod.

In one particular embodiment of instant invention the epicyclic gearbox releasibly connects the dose dial sleeve to the drive sleeve, whereby the ring gear is optionally located at the second end of the dose dial sleeve.

Optionally, the epicyclic gearbox is designed to give a radial velocity reduction ratio between the ring gear and the component carrying the planetary gear(s), which is optionally the drive sleeve.

In another specific embodiment of instant invention the sun gear is located between the dose button and the drive sleeve.

The term "first end" according to instant invention shall mean the proximal end. The proximal end of the device or a component of the device shall mean the end, which is closest to the dispensing end of the device.

The term "second end" according to instant invention shall mean the distal end, The distal end of the device or a component of the device shall mean the end, which is furthest away from the dispensing end of the device.

A second aspect of instant invention provides an assembly for use in a drug delivery device comprising the drive mechanism according to instant invention.

A third aspect of the present invention provides a drug delivery device comprising the drive mechanism or the assembly according to instant invention.

A fourth aspect of the present invention provides a method of assembling a drug delivery device comprising the step of providing a drive mechanism or an assembly according to instant invention.

A fifth aspect of instant invention is the use of a drug delivery device according to instant invention for dispensing a medicinal product preferably dispensing a pharmaceutical formulation (e.g. solution, suspension etc.) comprising an active compound selected from the group consisting of insulin, growth hormone, low molecular weight heparin, their analogues and their derivatives.

BRIEF DESCRIPTION OF THE DRAWINGS

Without any limitation, the instant invention will be explained in greater detail below in connection with a preferred embodiment and with reference to the drawings in which.

Figure 1:
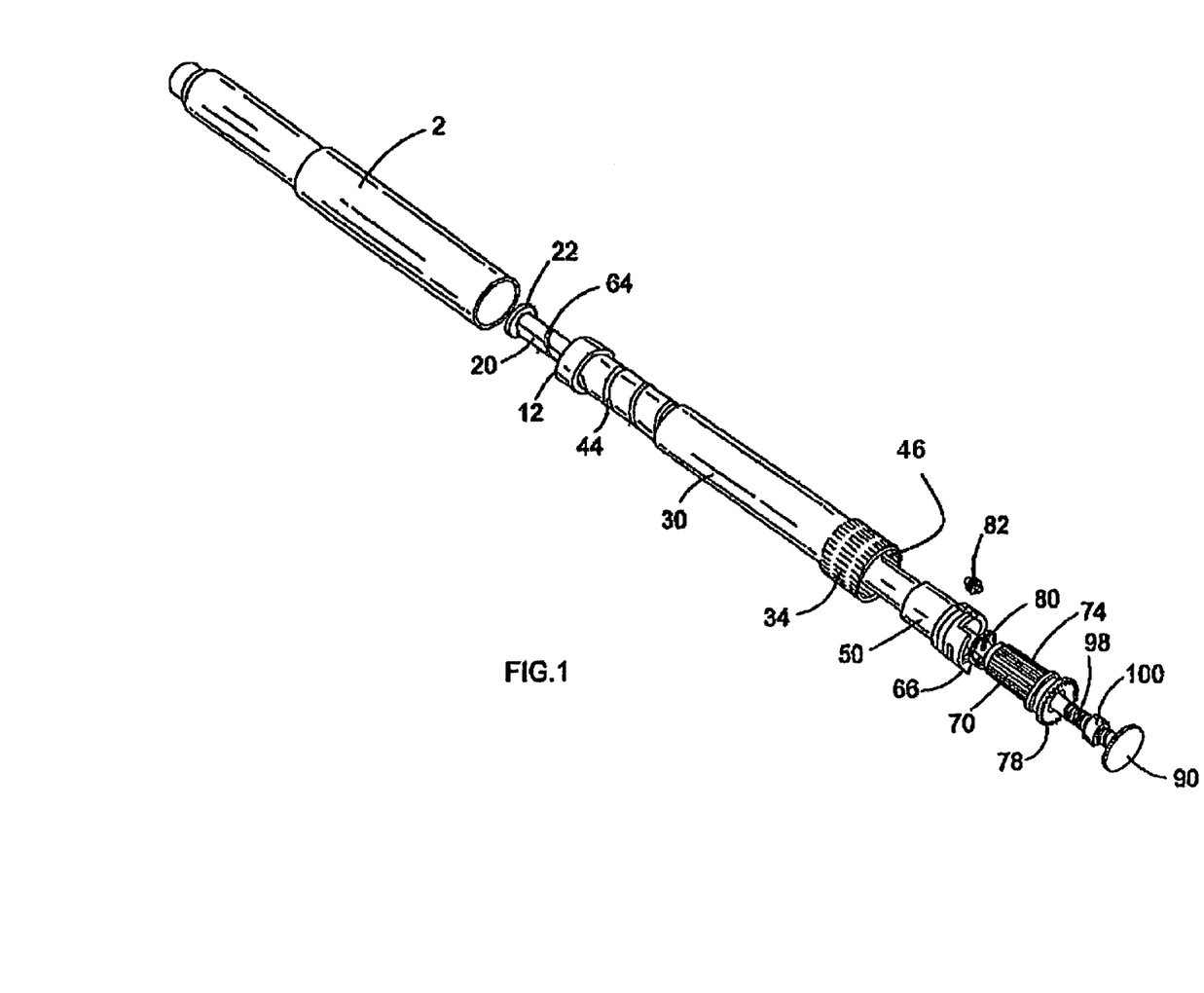
FIG. 1 shows an exploded view of the components of a drug delivery device in accordance with the present invention.
Figure 2:
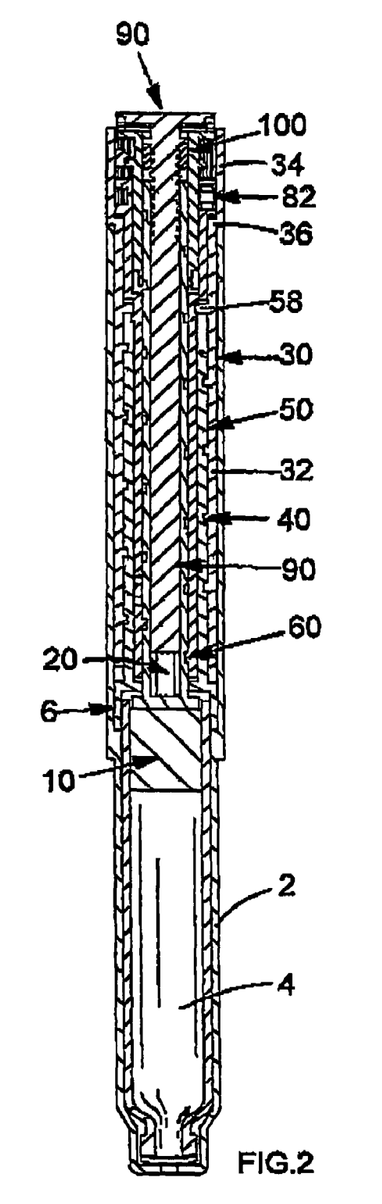
FIG. 2 shows a sectional side view of a drug delivery device in accordance with the present invention in a first unused position.

Referring first to FIG. 1 and FIG. 2 there may be seen a drug delivery device in accordance with the present invention. The device comprises a housing 2 within which are located a cartridge 4 containing a medicinal product, means for selecting or setting of the dose of medicinal product to be expelled and means for expelling the selected dose of medicinal product. The housing 2 is generally cylindrical in shape and is generally divided into two compartments by an insert 6 to be described in more detail below. The cartridge 4 is located within a first part of the housing 2 while the dose setting means and the means for expelling the selected dose of medicinal product are located within a second part of the housing 2.

The cartridge 4 may be secured in position in the first part of the housing 2 by any suitable means. A needle unit (not shown) may be secured to a first end of the housing 2. The cartridge 4 further comprises a displaceable piston 10. Advancing the piston 10 towards the first end of the cartridge 4 causes the medicinal product to be expelled from the cartridge 4 through the needle unit. A cap may be provided to cover the needle unit when the device is not in use.

The insert 6 dividing the housing 2 comprises a web extending radially inwards from the cylindrical housing to define an opening 8. A longitudinally extending skirt 12 extends from an outer periphery of the web. In use, the skirt 12 is secured in position to the housing 2 by any suitable means. A generally cylindrical portion 14 extends from the web towards a second end of the device. A piston rod 20 extends through the opening 8 in the insert 6.

The piston rod 20 comprises an end face 22 in use adapted to drive a second face of the piston 10 and a shaft or generally cylindrical part 24 extending longitudinally towards a second end of the device.

A generally cylindrical dose dial sleeve 30 comprises a first part 32 of smaller diameter disposed between the generally cylindrical portion of the insert 6 and the housing 2 and a second part 34 of larger diameter extending beyond the housing 2. Preferably, as in the illustrated embodiment the second pad 34 is of equal diameter to the housing 2 such that when the device is not in use a smooth overall impression is produced. The first part 32 and second part 34 of the dose dial sleeve 30 are connected by a radially extending annular region 36 of the dose dial sleeve 30.

An inner surface of the first part 32 of the dose dial sleeve 30 is provided with an inwardly directed flange 38. A threaded connection 40 is provided between the dose dial sleeve 30 and the insert 6. In the illustrated embodiment a helical rib 42 is provided on an inner face of the first part 32 of the dose dial sleeve 30 between a first end of the dose dial sleeve 30 and the inwardly directed flange 38. In this embodiment the helical rib 42 rests within a matched groove 44 provided on an outer surface of the insert 6.

An inner surface of the second part 34 of the dose dial sleeve 30 is provided with splines 46 in the form of longitudinally extending gear teeth. The splines 46 may serve as a ring gear of the epicyclic gearbox. The outer surface of the second part 34 of the dose dial sleeve 30 is preferably provided with a textured surface to serve as a finger grip.

A generally cylindrical drive sleeve 50 is disposed within the dose dial sleeve 30. The drive sleeve 50 comprises a first part 52 of smaller diameter generally disposed between the generally cylindrical portion 14 of the insert 6 and the piston rod 20 and a second part 54 of larger diameter extending beyond the inwardly directed flange 38 of the dose dial sleeve 30. The first and second parts 52, 54 of the drive sleeve 50 are connected by a radially extending annular region 56 of the drive sleeve 50.

The drive sleeve 50 and the dose dial sleeve 30 are held against relative longitudinal displacement by snap fit features 58 on the first part 52 of the drive sleeve 50 that locate the inwardly directed flange 38 of the dose dial sleeve 30 between the snap fit features 58 and the annular region 56 of the drive sleeve 50. It will be understood that relative rotation between the dose dial sleeve 30 and the drive sleeve 50 remains possible.

A threaded connection 60 is provided between the drive sleeve 50 and the piston rod 20. In the illustrated embodiment a helical rib 62 is provided on an inner face of the first part 52 of the drive sleeve 50. In this embodiment, the helical rib 62 rests within a groove 64 extending along an outer surface of the shaft 24 of the piston rod 20.

A generally cylindrical sun gear 70 is located within the second part 54 of the drive sleeve 50. The inner diameter of the sun gear 70 is sufficient to allow the shaft 24 of the piston rod 20 to pass therethrough. The outer surface of the sun gear 70 is split into two portions by a radially extending flange 72. Splines 74 extend from a first end of the sun gear 70 to the radial flange 72. A second radial flange 76 is disposed at the second end of the sun gear 70. The second radial flange 76 is provided on a second surface with a plurality of circumferentially extending teeth 78.

The second part 54 of the drive sleeve 50 extends within the first part 32 of the dose dial sleeve 30 and into the second part 34 of the dose dial sleeve 30. Spring means 80 are disposed between the annular region 56 of the drive sleeve 50 and a first end of the sun gear 70. That part of the drive sleeve 50 extending into the second part 34 of the dose dial sleeve 30 carries a planetary gear 82. The planetary gear 82 is mounted for rotation on a journal integral with the drive sleeve 50. The second end of the drive sleeve 50 is also provided with a spring feature 66, a free end of the spring feature 66 having an outwardly directed tooth 68.

A moulded clutch feature on the drive sleeve 50 operates between the drive sleeve 50 and the dose dial sleeve 30. The clutch is formed between the outer tooth 68 of the spring feature 66 and the splines 46 on the dose dial sleeve 34. When the device is not in use, or a dose is being dialed, the radially extending flange 72 holds the tooth 68 in position to engage with the splines 46, thereby locking the drive sleeve 50 to the dose dial sleeve 30 in rotation. During dispense, axial displacement of the flange 72 disengages the clutch, thereby allowing the drive sleeve 50 to rotate with respect to the dose dial sleeve 30.

The planetary gear 82 is provided about an outer surface with longitudinally extending gear teeth.

A generally cylindrical dose button 90 has a shaft 92 and a first radially extending flange 94 at a second end of the shaft 92. The shaft 92 of the dose button 90 is disposed within shaft 24 of the piston rod 20 for longitudinal but not rotational displacement with respect to the piston rod 20. Conveniently, this may be achieved by splining the dose button 90 to the piston rod 20. A threaded portion 98 is provided along at least a part of the shaft 92 and a second radial flange 96 is disposed between the threaded portion 98 and the first flange 94.

A first face of the first dose button flange 94 and a second face of the second sun gear flange 76 are provided with features which when mated together secure the dose button 90 and sun gear 70 against relative rotation.

Figure 4:
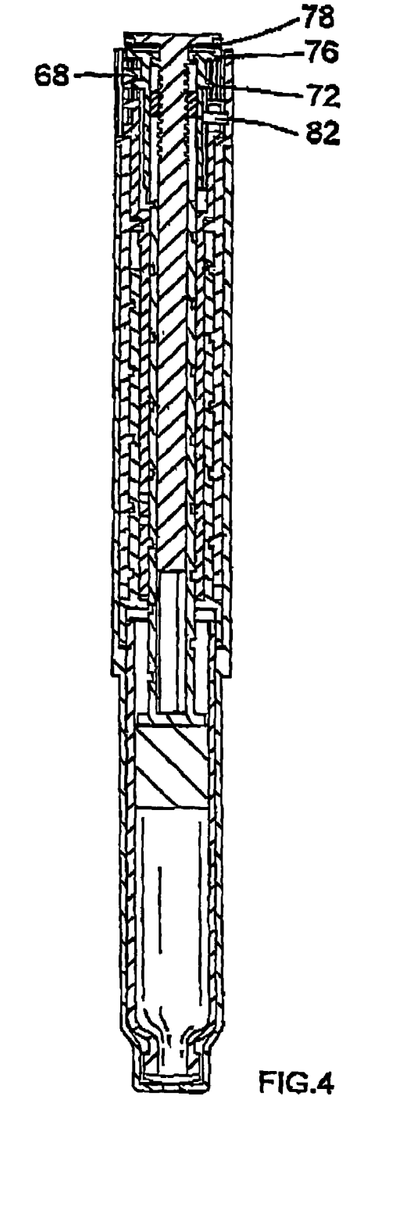
FIG. 4 shows a sectional side view of the drug delivery device of FIG. 1 in a third position following dispense of the first selected dose.

A nut 100 is provided on the threaded portion 98 between the dose dial button 90 and the sun gear 70. The nut 100 is coupled to the sun gear 70 by splines. Operation of the device will now be described. To set a desired dose to be delivered a user rotates the second part 34 of the dose dial sleeve 30. In the initial position (FIG. 2 or FIG. 4) the dose dial sleeve 30, the drive sleeve 50 and the sun gear 70 are coupled together by the spring feature 66 and rotate together as the dose dial sleeve 30 is turned. With the clutch means engaged, the drive sleeve 50 and the dose dial sleeve 30 are coupled together and the planetary gear 82 cannot rotate. This in turn couples the sun gear 70 to the dose dial sleeve 30 and the drive sleeve 50. A shoulder on the sun gear 70 locks the drive sleeve clutch means to the dose dial sleeve 30. The spring means 80 pushes the sun gear 70 into a position in which the outwardly directed tooth 68 of the drive sleeve 50 is locked for rotation to the splines 46 of the dose dial sleeve 30.

Relative rotational movement between the dose button 90 and the sun gear 70 causes the nut 100 to advance along the threaded portion 98 of the dose button shaft 92. When the nut 100 reaches the end of the threaded portion 92 (as in FIG. 5) the user is prevented from rotating the dose button 90, that is from dialing any further dose.

The threaded connection 40 between the insert 6 and the dose dial sleeve 30 has the same lead as the threaded connection 60 between the piston rod 20 and the drive sleeve 30. This means that when the dose dial sleeve 30 is rotated the piston rod 20 remains in contact with the second face of the cartridge piston 10.

Figure 3:
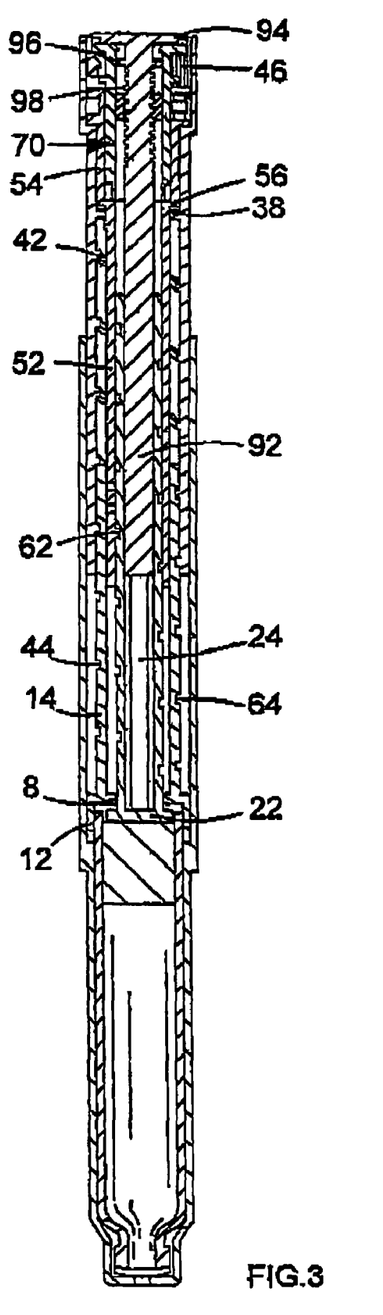
FIG. 3 shows a sectional side view of the drug delivery device of FIG. 1 in a second position when a first dose has been selected and a dispense action has just been started.
Figure 5:
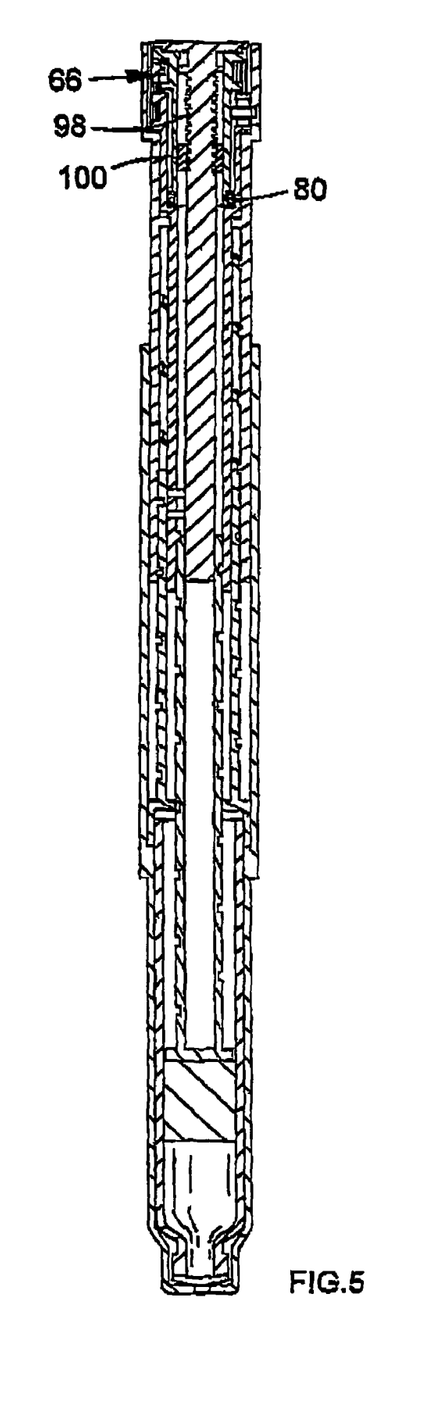
FIG. 5 shows a sectional side view of the drug delivery device of FIG. 1 in a fourth position corresponding to the setting of a maximum final dose when a dispense action has just been started.
Figure 6:
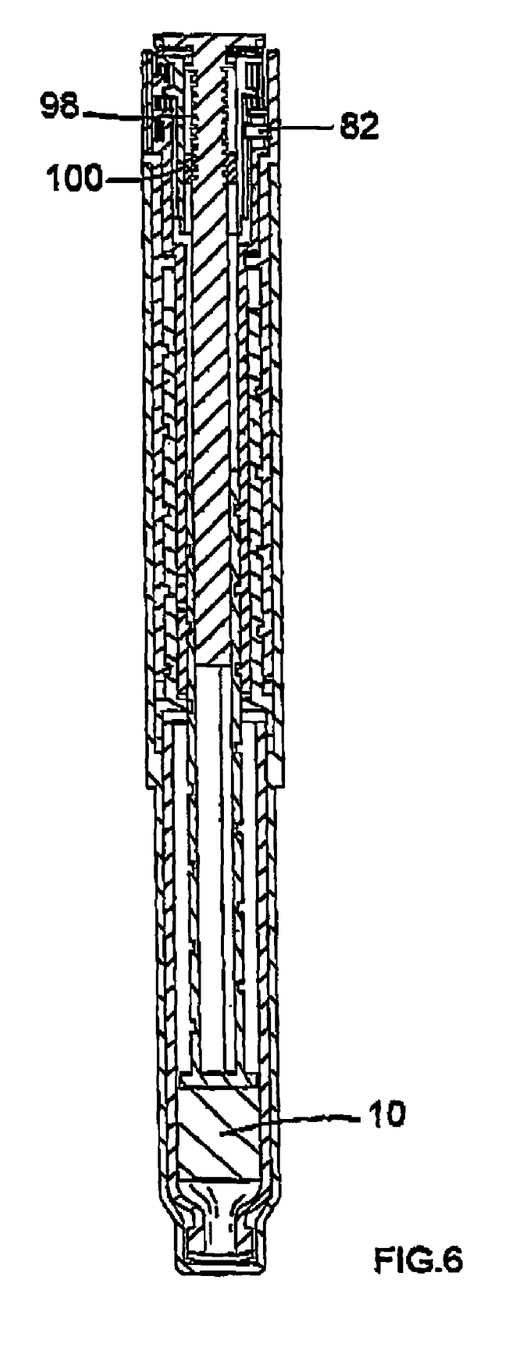
FIG. 6 shows a sectional side view of the drug delivery device of FIG. 1 in a final end of life position when the final dose has been dispensed.

To dispense a selected dose, a user depresses the dose button 90 (FIG. 3 or FIG. 5). Displacing the dose button 90 towards the first end of the device couples the dose button 90 to the sun gear 70 to lock the sun gear 70 in rotation to the dose button 90. The longitudinal movement of the sun gear 70 causes the spring means 80 to be compressed. The shoulder on the sun gear 70 locking the clutch means between the drive sleeve 50 and the dose dial sleeve 30 is disengaged, thereby allowing the drive sleeve 50 to rotate with respect to the dose dial sleeve 30. The planetary gear 82 then creates a gear ratio between the sun gear 70 and the dose dial sleeve 30.

Further depression of the dose button 90 causes an axial load to be applied to the sun gear 70. Under this axial load the dose dial sleeve 30 rotates against the thread of the insert 6 towards the first end. The sun gear 70 is locked to the dose button by means of the circumferential teeth 78 and therefore causes the drive sleeve 50 to rotate at a different angular velocity than the dose dial sleeve 30 by action of the epicyclic gearbox. The rotation of the drive sleeve 50 causes the piston rod 20 to advance towards the first end by means of the threaded engagement between the drive sleeve 50 and the piston rod 20.

The invention claimed is:

1. A drive mechanism for a drug delivery device comprising:
   an epicyclic gearbox;
   a piston rod including a non-circular cross-section and an external helical thread; and
   a drive sleeve configured to engage with the external helical thread of the piston rod;
   wherein the drive sleeve is configured to be disposed between a housing and the piston rod.

2. The drive mechanism of claim 1, wherein the drive sleeve is configured to be releasably connected to a dose dial sleeve via the epicyclic gearbox.

3. An assembly for use in a drug delivery device, comprising:
   a drive mechanism including an epicyclic gearbox, a piston rod including a non-circular cross-section and an external helical thread, and a drive sleeve configured to engage with the external helical thread of the piston rod;
   a housing including a helical thread; and
   a dose dial sleeve configured to engage with the helical thread of the housing and configured to rotate relative to the housing;
   wherein the drive sleeve is configured to be disposed between the housing and the piston rod.

4. The assembly of claim 3, wherein the dose dial sleeve is configured to be releasably connected to the drive sleeve via the epicyclic gearbox.

5. A drug delivery device, comprising:
   a drive mechanism including an epicyclic gearbox, a piston rod including a non-circular cross-section and an external helical thread, a drive sleeve configured to engage with the external helical thread of the piston rod;
   a housing including a helical thread, a portion of the housing configured to receive a medicinal product to be delivered; and
   a dose dial sleeve configured to engage with the helical thread of the housing and configured to rotate relative to the housing;
   wherein the drive sleeve is configured to be disposed between the housing and the piston rod.

6. The drug delivery device of claim 5, wherein the dose dial sleeve is configured to be releasably connected to the drive sleeve via the epicyclic gearbox.

7. A method of assembling a drug delivery device, comprising:
   providing a drive mechanism including an epicyclic gearbox, a piston rod including a non-circular cross-section and an external helical thread, and a drive sleeve;
   providing a housing including a helical thread;
   providing a dose dial sleeve configured to rotate relative to the housing;
   engaging the dose dial sleeve with the helical thread of the housing;
   placing the drive sleeve between the housing and the piston rod; and
   engaging the drive sleeve with the external helical thread of the piston rod.

8. The method of claim 7, further comprising:
   releasably connecting the dose dial sleeve to the drive sleeve via the epicyclic gearbox.

9. A method of assembling a drug injection device, comprising:
   providing a housing having a first portion and a second portion, the first portion of the housing being configured to receive a cartridge containing a medicinal product to be dispensed;
   providing an assembly including a drive mechanism including an epicyclic gearbox and a piston rod including a non-circular cross-section and an external helical thread in the second portion of the housing.

10. A method of assembling a drug delivery device, comprising:
    providing an assembly including a drive mechanism including an epicyclic gearbox, a piston rod including a non-circular cross-section and an external helical thread, and a drive sleeve;
    providing a housing including a helical thread;
    providing a dose dial sleeve configured to rotate relative to the housing;
    engaging the dose dial sleeve with the helical thread of the housing;
    placing the drive sleeve between the housing and the piston rod; and
    engaging the drive sleeve with the external helical thread of the piston rod.

11. The method of claim 10, further comprising:
    releasably connecting the dose dial sleeve to the drive sleeve via the epicyclic gearbox.

12. A method of dispensing a medicinal product, comprising:
    providing a drug delivery device including a drive mechanism including an epicyclic gearbox and a piston rod including an external helical thread; and
    dispensing the medicinal product via the drug delivery device;
    wherein the medicinal product includes an active ingredient selected from the group consisting of insulin, growth hormone, low molecular weight heparin, analogues of insulin, analogues of growth hormones, analogues of low molecular weight heparin, derivatives of insulin, derivatives of growth hormones, and derivatives of low molecular weight heparin.

13. The method of claim 12, wherein the drive mechanism further includes a drive sleeve configured to engage with the external helical thread of the piston rod;
    wherein the drug delivery device further includes a housing including a helical thread; and
    a dose dial sleeve configured to engage with the helical thread of the housing and configured to rotate relative to the housing;
    wherein the drive sleeve is disposed between the housing and the piston rod; and
    wherein dispensing the medicinal product further includes selectively rotating the dose dial sleeve relative to the drive sleeve.

14. The method of claim 13, wherein the dose dial sleeve is configured to be releasably connected to the drive sleeve via the epicyclic gearbox.

15. The method of claim 12, wherein the piston rod further includes a non-circular cross-section.

* * * * *